(12) United States Patent
Eramo

(10) Patent No.: US 7,534,495 B2
(45) Date of Patent: May 19, 2009

(54) LUBRICIOUS COMPOSITION

(75) Inventor: Lincoln Eramo, Winchester, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 683 days.

(21) Appl. No.: 10/767,986

(22) Filed: Jan. 29, 2004

(65) Prior Publication Data

US 2005/0170071 A1 Aug. 4, 2005

(51) Int. Cl.
   B32B 27/08 (2006.01)
   C09D 133/14 (2006.01)

(52) U.S. Cl. ............... 428/424.2; 428/515; 522/39; 522/44; 522/46; 522/121; 522/142

(58) Field of Classification Search ............... 522/84, 522/85, 121, 142, 39, 44, 46; 428/424.2, 428/515
   See application file for complete search history.

(56) References Cited

U.S. PATENT DOCUMENTS

| | | | | |
|---|---|---|---|---|
| 4,439,583 A * | 3/1984 | Gould et al. | ............... | 525/127 |
| 5,091,205 A | 2/1992 | Fan | ............... | 427/2 |
| 5,429,590 A * | 7/1995 | Saito et al. | ............... | 602/48 |
| 5,441,488 A | 8/1995 | Shimura et al. | ............... | 604/265 |
| 5,503,631 A | 4/1996 | Onishi et al. | ............... | 604/96 |
| 5,509,899 A | 4/1996 | Fan et al. | ............... | 604/96 |
| 5,558,900 A | 9/1996 | Fan et al. | ............... | 427/2.28 |
| 5,573,934 A * | 11/1996 | Hubbell et al. | ............... | 435/177 |
| 5,576,072 A | 11/1996 | Hostettler et al. | ............... | 427/532 |
| 5,620,738 A | 4/1997 | Fan et al. | ............... | 427/2.3 |
| 5,645,931 A | 7/1997 | Fan et al. | ............... | 428/334 |
| 5,662,960 A | 9/1997 | Hostettler et al. | ............... | 427/2.3 |
| 5,667,735 A * | 9/1997 | Bae et al. | ............... | 264/1.7 |
| 5,670,558 A | 9/1997 | Onishi et al. | ............... | 523/112 |
| 5,693,034 A | 12/1997 | Buscemi et al. | ............... | 604/265 |
| 5,731,087 A | 3/1998 | Fan et al. | ............... | 428/412 |
| 5,756,144 A | 5/1998 | Wolff et al. | ............... | 427/2.3 |
| 5,849,368 A | 12/1998 | Hostettler et al. | ............... | 427/536 |
| 5,902,631 A | 5/1999 | Wang et al. | ............... | 427/2.1 |
| 5,919,570 A | 7/1999 | Hostettler et al. | ............... | 428/424.8 |
| 5,936,005 A * | 8/1999 | Askienazy et al. | ............... | 522/120 |
| 6,017,577 A | 1/2000 | Hostettler et al. | ............... | 427/2.12 |
| 6,030,656 A | 2/2000 | Hostettler et al. | ............... | 427/2.3 |
| 6,040,058 A | 3/2000 | Hostettler et al. | ............... | 428/457 |
| 6,048,620 A | 4/2000 | Zhong | ............... | 428/424.4 |
| 6,080,488 A | 6/2000 | Hostettler et al. | ............... | 428/423.3 |
| 6,114,406 A * | 9/2000 | Caiger et al. | ............... | 522/121 |
| 6,120,904 A | 9/2000 | Hostettler et al. | ............... | 428/423.3 |
| 6,161,630 A | 12/2000 | Stump et al. | ............... | 175/26 |
| 6,176,849 B1 | 1/2001 | Yang et al. | ............... | 604/265 |
| 6,221,425 B1 | 4/2001 | Michal et al. | ............... | 427/2.25 |
| 6,221,467 B1 | 4/2001 | Nazarova et al. | ............... | 428/213 |
| 6,262,115 B1 | 7/2001 | Guittard et al. | ............... | 514/534 |
| 6,265,016 B1 | 7/2001 | Hostettler et al. | ............... | 427/2.11 |
| 6,436,540 B1 * | 8/2002 | Garcia et al. | ............... | 428/423.1 |
| 6,458,867 B1 | 10/2002 | Wang et al. | ............... | 523/105 |
| 6,503,958 B2 | 1/2003 | Hughes et al. | ............... | 521/64 |
| 6,506,823 B2 * | 1/2003 | Burns et al. | ............... | 524/35 |
| 6,528,150 B2 | 3/2003 | Nazarova et al. | ............... | 428/212 |
| 6,540,698 B1 | 4/2003 | Ishii | ............... | 600/585 |
| 6,589,215 B2 | 7/2003 | Yang et al. | ............... | 604/265 |
| 6,610,035 B2 | 8/2003 | Yange et al. | ............... | 604/265 |
| 6,648,874 B2 | 11/2003 | Parisi et al. | ............... | 604/525 |
| 6,656,517 B2 | 12/2003 | Michal et al. | ............... | 427/2.24 |
| 6,673,053 B2 | 1/2004 | Wang et al. | ............... | 604/265 |
| 6,673,453 B2 | 1/2004 | Beavers et al. | ............... | 428/420 |
| 7,012,057 B2 * | 3/2006 | Kapoor et al. | ............... | 510/440 |
| 2004/0151930 A1* | 8/2004 | Rouns et al. | ............... | 428/500 |
| 2005/0054774 A1* | 3/2005 | Kangas | ............... | 525/123 |
| 2005/0055044 A1* | 3/2005 | Kangas | ............... | 606/194 |

OTHER PUBLICATIONS

Kapoor et al, "Improvements Relating to Detergent Bars", WO 03/046119 A1, Jun. 5, 2003.*
Sartomer "*Trifunctional Acrylate Backbone Structure Physical Properties*" Sartomer Company, Inc., No. 5080; Nov. 2001.
Sartomer "*Application Bulletin*" Sartomer Company, Inc., No. 4001; Apr. 2002.
U.S. Appl. No. 10/658,718, filed Sep. 9, 2003, Steve Kangas.
U.S. Appl. No. 10/658,729, filed Sep. 9, 2003, Steve Kangas.

* cited by examiner

*Primary Examiner*—Susan W Berman
(74) *Attorney, Agent, or Firm*—Vidas, Arrett & Steinkraus, P.A.

(57) ABSTRACT

A lubricious composition suitable for use on medical device, the composition including at least one alkoxylated acrylate compound having at least two acrylate groups per molecule and at least one second component which provides lubricity.

45 Claims, No Drawings

LUBRICIOUS COMPOSITION

BACKGROUND OF THE INVENTION

The present invention relates to the field of lubricious compositions useful as coatings on surfaces of medical devices.

Improving the surface lubricity of insertable medical devices such as by application of lubricious polymeric coatings to the surfaces of such devices for the purpose of reducing friction between the surface of the medical device and other surfaces to which it comes into contact, such as when the device is introduced into the human body, is known in the art.

Catheters used for the delivery of other medical devices such as stents, stent-grafts, grafts, vena cava filters, dilatation balloons, as well as other expandable medical devices, and other medical devices used for introduction in blood vessels, urethra, body conduits and the like, and guide wires used with such devices are examples of articles which may be provided with lubricious coatings.

Guide catheters, and catheters for balloon angioplasty and biopsy are specific examples of such catheters.

Lubricious coatings of both a hydrophobic and a hydrophilic nature are known. Silicone is an example of a known hydrophobic lubricant.

Hydrogel polymers are also known lubricants and may be characterized by an initial non-tacky to tacky quality followed by lubricity upon hydration.

SUMMARY OF THE INVENTION

The present invention relates to lubricious compositions useful for coating medical devices including at least one polymerizable component which is an alkoxylated acrylic based compound having at least two acrylate groups, and suitably three or more acrylate groups per molecule. The present invention also contemplates the use of the methacrylates as well.

As used herein, the term "compound" shall refer to monomers, oligomers and polymers.

The amount of alkoxylation is suitably about 1 to about 20 moles alkoxylate, more suitably about 2 to about 18 moles of alkoxylate, and more suitably about 3 to about 15 moles alkoxylate. Examples of alkoxylates include propoxylates and ethoxylates, as well as mixtures thereof.

Desirably, the alkoxylated (meth)acrylate compounds are non-aromatic alkoxylated (meth)acrylate compounds.

Suitably, the alkoxylated (meth)acrylate compounds have some water solubility of greater than about 15 wt-% and desirably even greater than about 50 wt-%.

In one embodiment, at least one alkoxylated trimethylol propane tri(meth)acrylate compound is employed in combination with at least one second component which provides lubricity.

One example of an alkoxylated trimethylol propane tri (meth)acrylate useful herein is ethoxylated trimethylol propane tri(meth)acrylate compound.

The second component may be any lubricious polymeric material, including lubricious hydrophobic lubricious polymers and hydrophilic lubricious polymers, as well as the hydrogels, or mixtures thereof. Crosslinkable materials may also be employed. Suitable polymers are disclosed in commonly assigned U.S. Pat. No. 5,693,034 which is incorporated by reference herein in its entirety.

In one aspect of the invention, the crosslinker is employed with a noncrosslinked lubricious hydrogel polymer.

The polymerizable (meth)acrylate compound may also be employed with highly water absorbent polyurethanes such as those disclosed in commonly assigned copending U.S. patent application Ser. No. 10/658,718 which is incorporated by reference herein in its entirety. Such polyurethanes, typically aliphatic polyether polyurethanes, may be highly water absorbent, being capable of absorbing anywhere from about 500% to about 2000% water by weight. These polymers may be advantageously blended with polyurethanes having lesser water absorbency.

In another aspect, the polymerizable component may be employed in combination with at least one second polymerizable component. Examples of these types of compositions may be found in commonly assigned copending U.S. patent application Ser. No. 10/658,729 which is incorporated by reference herein in its entirety.

The above types of compositions often form what is referred to in the art as "semi-interpenetrating polymer networks" or "interpenetrating polymer networks".

A photoinitiator may be advantageously incorporated in the compositions of the present invention to facilitate crosslinking of the alkoxylated (meth)acrylate compound. Any suitable initiator used in combination with (meth)acrylates may be employed herein. Free radical type photoinitiators including, but not limited to, benzophenones, ketones, acrylated amine synergists, α-amino ketones, benzil ketals, find utility herein.

In one embodiment, at least one amino substituted ketone is employed. Examples of suitable α-amino ketones include, for example, 2-methyl 1-[4-methylthio) phenyl]2-morpholinopropan-1-one, 2-benzyl-2-(dimethylamine)-1-[4-morpholinyl)phenyl]-1-butanone.

Other optional additives may also be employed including, but not limited to, fillers, flow or viscosity modifiers, coupling agents, adhesion promoters, antioxidants, and so forth. Such additives are known to those of ordinary skill in the art.

Of course, mixtures of any of the above materials may be employed in the composition as well.

The lubricious composition may be applied on the surface of medical devices or components thereof including polymeric and metallic surfaces to provide lubricity to such surfaces. The lubricious coatings find particular utility on medical devices and components thereof such as catheter shafts, guidewires, guidewire lumens, dilatation balloons, stent retaining sleeves, and so forth. Inner and outer surfaces and combinations thereof may be coated. The lubricious coatings may be employed on both inner and outer surfaces of such medical devices and components thereof.

In one embodiment, the medical device is a catheter device such as a guide catheter or a delivery catheter.

However, the lubricious coatings according to the present invention find utility for reducing frictional forces of any medical devices insertable in the body of a patient where one surface is movably in contact with another surface.

The surface of the device to which the lubricious composition of the present invention is to be applied may also first be primed or otherwise treated to improve the adhesion of the lubricious composition to the surface of the device. Such primers or treatments are known to those of skill in the art and include, amount others, coupling agents, primer compositions and plasma or corona treatments, for example.

The present invention further relates to a process for applying the lubricious coatings to the medical devices or components thereof. Such method includes the steps of applying the coating to the device or component thereof, and polymerizing the polymerizable material(s) on the surface of the device by administering UV radiation to the coated surface of the device. Application of the coating may be accomplished out of solvent by spraying, brushing, painting, or so forth. Useful solvents include, but are not limited to, water, lower alcohols such as isopropanol, methanol and so forth. Extrusion, coextrusion, and other application techniques may also be employed depending on the properties of the lubricant which is being used. Such techniques do not require the use of solvents.

Other benefits and advantages and will become apparent from the following description.

All patents discussed herein are incorporated by reference herein in their entirety.

DETAILED DESCRIPTIONS OF THE INVENTION

While this invention may be embodied in many different forms, there are described in detail herein specific embodiments of the invention. This description is an exemplification of the principles of the invention and is not intended to limit the invention to the particular embodiments illustrated.

The present invention relates to a lubricious composition which may be employed on the surfaces of medical devices for reducing the friction between the lubricated surface, and at least one second surface.

The lubricious composition according to the invention includes at least one alkoxylated (meth)acrylate having at least two acrylate or methacrylate groups, and suitably three or more (meth)acrylate groups. The amount of alkoxylation is suitably from about 1 to about 20 moles, more suitably about 2 to about 20 moles, and even more suitably about 3 to about 20. It is more desirable having about 2 to about 18 moles of alkoxylation and most desirable having about 3 to about 15 moles of alkoxylation. Examples of suitable alkoxylate groups include both propoxylates and ethoxylates as well as mixtures thereof.

Examples of suitable bi-, tri-, tetra-, etc. polyfunctional alkoxylated or polyalkoxylated acrylates include alkoxylated, desirably ethoxylated or propoxylated, neopentyl glycol diacrylates, butanediol diacrylates, trimethylolpropane tri-acrylates glyceryl triacrylates; and so forth.

In one embodiment, an alkoxylated trimethylol propane triacrylate monomer is employed, suitably an ethoxylated trimethylol propane triacrylate. Such compounds are available from Sartomer Company, Inc. in Exton, Pa. Examples include SR454 having 3 moles of ethoxylation, a molecular weight of 454 g/mole and a water solubility of 15 wt-% in water; SR499 having 6 moles of ethoxylation and a molecular weight of 560 g/mole; SR502 having 9 moles of ethoxylation and a molecular weight of 693 g/mole and SR9035 having 15 moles of ethoxylation and a molecular weight of 956 g/mole. Such compounds may also be found from Aldrich Chemical Co., Inc. in Milwaukee, Wis. having from 1 mole of alkoxylate and greater.

Other examples of suitable alkoxylated (meth)acrylate compounds include, but are not limited to, propoxylated trimethylol propane tri(meth)acrylate, ethoxylated pentaerythritol tetra(meth)acrylate, propoxylated neopentyl glycol diacrylate, propoxylated gylceryl tri(meth)acrylate, trimethylolpropane ethoxylate (1 EO/OH) methyl ether diacrylate, and so forth.

Suitably, the alkoxylated (meth)acrylate compounds have some water solubility of about 15 wt-% or more, and even more desirably, about 50 wt-% or more.

The aromatic alkoxylated (meth)acrylates tend to have little or no water solubility. For example, ethoxylated bisphenol A di(meth)acrylate, is classified as alkali soluble. However, this is not to say that some of the aromatic acrylates do not have water solubility and thus, if so, they may also be employed herein.

These acrylate compounds may be employed in amounts of about 0.1 wt-% to about 5 wt-%, and even more typically about 0.1 wt-% to about 2 wt-% based on a solvent or cosolvent blend.

The polymerizable materials are typically cured through the addition of actinic radiation such as ultraviolet (UV) radiation, e-beam radiation, or laser beam radiation may also be employed. The ethoxylated (meth)acrylate compounds, for the most part, cure via a free radical mechanism. They also may be sensitive to oxygen and can form stable radicals in its presence. Thus, it may be advantageous to employ an inert gas purge.

Crosslinking may be facilitated by the addition of a small amount of a photoinitiator. Any photoinitiator which is suitable for use in free radical curing mechanisms may be employed herein. Examples of suitable photoinitiators include, but are not limited to, benzophenones, acrylated amine synergists, ketone type, i.e. aromatic-aliphatic ketone derivatives, including benzoin and its derivatives, benzil ketals, α-amino ketones, and so forth.

More specific examples of photoinitiators suitable for use herein include, but are not limited to, 2-phenyl-1-indanone; IRGACURE® 184 from Ciba Specialty Chemicals, BENACURE® 184 from Mayzo and SARCURE® SR1122 from Sartomer, all of which are 1-hydroxylcyclohexylphenyl ketone (HCPK); BENACURE® BP benzophenone; BENACURE® 651 and IRGACURE® 651, both of which are benzil dimethyl ketal or 2,2' dimethoxy-2-phenylacetophenone; BENACURE® 1173 2-hydroxy-2-methyl-1-phenyl-1-propanone; IRGACURE® 907 2-methyl 1-[4-methylthio)phenyl]2-morpholinopropan-1-one; IRGACURE® 369 morpholinoketone; and so forth and blends thereof.

Photoinitiators are also available commercially in a variety of blends. Examples of commercially available blends include, but are not limited to, SARCURE® SR1136 is a blend of 4-methylbenzophenone and benzophenone; SARCURE® SR1137 is a blend of trimethylbenzophenone and methylbenzophenone; BENACURE® 500, a blend of 1-hydroxylcyclohexylphenyl ketone and benzophenone;

The above lists are intended for illustrative purposes only, and not as a limitation on the scope of the present invention. One of ordinary skill in the art has knowledge of such photoinitiators.

Particularly suitable for use in combination with the (meth) acrylate type compounds of the present invention include the ketone type photoinitiators and the α-amino ketones.

In one embodiment, at least one α-amino ketone photoinitiator is employed. Examples of suitable α-amino ketone photoinitiators include, but are not limited to, 2-methyl 1-[4-methylthio) phenyl]2-morpholinopropan-1-one, 2-benzyl-2-(dimethylamine)-1-[4-morpholinyl)phenyl]-1-butanone or a mixture thereof.

It has been found by the present inventors, that the α-amino ketone photoinitiators may be employed advantageously with any ethylenically unsaturated monomer and second lubricity providing component to arrive at an improved photocurable interpenetrating network. See for example, commonly assigned copending U.S. patent application Ser. No. 10/658,729, the entire content of which is incorporated by reference herein in its entirety.

Mixtures of any of the above photoinitiators may also be employed. Photoinitiators or blends thereof are typically used in amounts of about 0.01 wt-% to about 5 wt-%.

In another aspect, the present invention relates to the use of α-amino ketone photoinitiators in combination with a polymerizablee ethylenically unsaturated resin and at least one second component which provides lubricity.

Other optional additives may be employed in combination with the present invention including, but not limited to, flow or viscosity modifiers, antioxidants, coupling agents, and so forth.

Any suitable component which provides sufficient lubricity and is acceptable for use on medical devices implantable or insertable in the human body, may find utility herein. Suitably, such lubricating materials are biocompatible materials.

Both hydrophilic and hydrophobic polymeric materials find utility herein, as well as the special subclass of lubricious materials referred to as the hydrogels, and combinations thereof. However, hydrophilic polymers are most desirable.

Suitable examples of hydrophilic lubricants, include, but are not limited to, polyalkylene glycols and alkoxy polyalkylene glycols; copolymers of methylvinyl ether and maleic acid; maleic anhydride polymers; polylkylene oxides, particularly the polyethylene oxides; poly((meth)acrylic acids); polymers of hydroxyl-substituted lower alkyl(meth)acrylates, such 2-hydroxyalkyl(meth)acrylate; polyvinylalcohols, hydrophilic polyamides; poly(meth)acrylamides; poly(N-isopoly(meth)acrylamides); poly(sodium-4-styrenesulfonates) and poly(sodium vinylsulfonates); poly(3-hydroxybutyric acids); poly(N-vinyl lactams) such as the polyvinylpyrrolidones; hydrophilic polyurethanes; polyethyleneimines; poly(sodium(meth)acrylates); methyl cellulose, hydroxylmethyl cellulose, hydroxyethyl cellulose; polyvinylsulfonic acid; heparin; dextran and dextan sulfate and other modified dextrans; poly(saccharides); chondroitin sulphate; lecithin; and so forth, as well as copolymers thereof, and mixtures thereof. As used herein for purposes of simplicity, the term "copolymer" shall be used to refer to any polymer formed from more than one compound including the copolymers, terpolymers and so forth. Hydrophilic lubricants are described in commonly assigned U.S. Pat. No. 6,458,867 which is incorporated by reference herein in its entirety.

Hydrophilic compounds are discussed in U.S. Pat. No. 6,503,958 which is incorporated by reference herein in its entirety.

Hydrophilic polyurethanes, typically aliphatic polyether polyurethanes, which have high water absorbency being capable of absorbing anywhere from about 500% to about 2000% water by weight, may be employed herein. These types of polyurethanes are described in commonly assigned copending U.S. patent application Ser. No. 10/658,718 which is incorporated by reference herein in its entirety. These polymers may be advantageously blended with polyurethanes having lesser water absorbency.

Hydrogel polymers find utility herein. The above list of hydrophilic lubricants include some of which may be classified as "hydrogels". Hydrogels are known to absorb water and become slippery upon exposure to an aqueous environment. Examples of the hydrogels include, but are not limited to, polyethylene oxide, polyacrylic acid, polyacrylamides, poly(sodium4-styrenesulfonates), poly(3-hydroxybutyric acids), polyvinylpyrrolidones, 2-hydroxyethyl methacrylates, and so forth. Hydrogels are known to those of ordinary skill in the art. Hydrogels are discussed in commonly assigned U.S. Pat. No. 5,693,034 which is incorporated by reference herein in its entirety.

Molecular weights may range anywhere from 1,000 g/mole to 1,000,000 g/mole or more. Suitably, the weight average molecular weight of such polymers is from about 75,000 g/mole to about 1,000,000 g/mole and more suitably about 100,000 g/mole to about 750,000 g/mole. See for example, U.S. Pat. No. 6,262,115 which discusses molecular weights of such hydrogels, the entire content of which is incorporated by reference herein in its entirety.

The above lists are intended for illustrative purposes only and not as a limitation on the present invention. One of ordinary skill in the art has knowledge of such hydrophilic polymeric materials.

Hydrophobic materials may be employed herein, although hydrophilic compounds are more desirable for use. Hydrophobic lubricants include, but are not limited to, silicones (i.e. organosiloxane polymers), functionalized silicones, hydrolyzable silanes which form silicones, fluorosilanes and other fluoropolymers, cellulose esters and ethers, ethyl cellulose, cellulose nitrate, cellulose acetate, cellulose acetate butyrate, cellulose acetate propionate, hydrophobic polyurethanes, polyacrylates, natural and synthetic elastomers, polyacetals, hydrophobic polyamides, polyvinylidene chloride, polycarbonate, homopolymers and copolymers of vinyl compounds, polyvinylchloride, glycerin, olive, vegetable, and other natural oils, and so forth. Some of these materials also form a gel-like substance, such as some silicones.

Molecular weights of the lubricants may range anywhere from 1,000 g/mole to 1,500,000 g/mole, desirably 50,000 to about 1,000,000 g/mole with those on the higher end being desirable.

Upon curing, the alkoxylated (meth)acrylate compounds may form what is referred to in the art as a "semi-interpenetrating network" or an "interpenetrating network" (IPN) with the lubricious material. Such networks may help to entrap the lubricious polymer on the surface to which it is applied.

Other optional ingredients may be incorporated into the compositions according to the invention including, but not limited to, flow or viscosity modifiers, antioxidants, coupling agents, surfactants, and so forth.

Examples of suitable flow modifiers include, but are not limited to, acrylic flow modifiers, fine silica powders, fine barium sulfate powders, fine particulate organic resins, clay-containing flow modifiers, polyamide-containing flow modifiers, urea-containing flow modifiers, urethane-containing flow modifiers, polycarboxylic acid salt-containing flow modifiers, cellulose-containing flow modifiers and so forth. Flow modifiers may be used in amounts of about 0.1 wt-% to about 5 wt-%, more suitably about 0.1 wt-% to about 1 wt-% and most suitably about 0.1 wt-% to about 0.2 wt-% based on a solvent or cosolvent blend of the composition.

Examples of suitable coupling agents include, but are not limited to, silanes, titanates, zirconates, and so forth. Coupling agents may be employed in amounts of about 0.01 wt-% to about 5 wt-%, more suitably about 0.01 wt-% to about 1 wt-%, and most suitably about 0.01 wt-% to about 0.1 wt-% based on a solvent or cosolvent blend of the composition.

The above lists are intended for illustrative purposes only and are not intended to limit the scope of the present invention. Other solvents not listed herein would find utility in the invention as well and are known to those of skill in the art.

In preparing the solution mixture of the present invention, the lubricity providing component and the ethylenically unsaturated resin or alkoxylated (meth)acrylate is admixed in a solvent or cosolvent mixture. Examples of suitable organic solvents of a more polar nature include, but are not limited to, the lower alcohols including, but not limited to, isopropyl alcohol and methanol; water; linear or cyclic carboxamides such ad N,N-dimethylacetamide (DMAC), N,N-diethylacetamide dimethylformamide (DMF), ethyl formamide, diethylformamide; N-methyl-2-pyrrolidone (NMP); dimethylsulphoxide (DMSO); acetonitrile; acetone and acetyl acetone; acrylonitrile; benzonitriledimethyl acetamide; 1,4-dioxane; dipropyl sulfone; aromatic solvents such as toluene and xylene; nitrobenzene; phenylacetate; propionitrile; and so forth.

Other suitable organic solvents include, but are not limited to, aliphatic, cycloaliphatic or aromatic ether-oxides, more particularly dipropyl oxide, diisopropyl oxide, dibutyl oxide, methyltertiobutylether, ethylene glycol dimethylether (glyme), diethylene glycol dimethylether (diglyme); phenyl oxide; dioxane, tetrahydrofuran (THF). Of course, any mixtures of the above-described solvents, i.e. cosolvent blends, may also be employed.

Examples of suitable solvents for use with hydrophobic lubricants include, but are not limited to, THF, chloroform, HFIP, DMF and so forth.

In the case of an alkoxylated (meth)acrylate monomer which 15 wt-% water solubility or more, water and lower alcohols may be satisfactorily employed as the solvent/cosolvent blend.

However, if an acrylate polymer is employed, it will be necessary to select a solvent based on the solubility of the acrylate polymer in the solvent/cosolvent blend. Such solvent selection is known to those of ordinary skill in the art.

If the lubricant is admixed in a solvent, the amount of lubricant is typically not more than about 5 wt-%, typically about 1 to about 5 wt-%. Of course, to some degree, this may depend on the viscosity of the polymer being employed.

The above list is intended for illustrative purposes only and not as a limitation on the scope of the present invention. One of ordinary skill in the art has knowledge of such solvents.

Surfactants may be advantageously employed to obtain a satisfactory mixture in the solvent or cosolvent blend. Any soluble surfactant or a mixture of surfactants in the above-mentioned solvents may be useful. Surfactants may be particularly advantageous where hydrophobic and hydrophilic materials, or other wise incompatible materials, are being admixed with one another.

The mixture may be applied to the medical device by any method known in the art including, but not limited to, spraying, dipping, painting, rolling, sponge painting, and so forth.

The coating will then be allowed to dry. The solvent may be more readily evaporated at an elevated temperature, although room temperature drying is acceptable. However, improved durability may be achieved by drying the coating at elevated temperatures of, for example, 70° C. Suitably, drying is conducted at an elevated temperature over several hours to improve the durability of the coating. Crosslinkers which have a high enough molecular weight and which are not highly volatile, can be compounded directly with lubricant, allowing the use of extrusion or coextrusion techniques for applying the coating. Such techniques do not require the use of solvents.

Once a coating has been applied to a substrate, the coating may then be crosslinked by exposing the coating to heat or actinic radiation such as UV light for a short period of time. This can then trigger the polymerization and crosslinking of the ethylenically unsaturated resin or prepolymer. Suitably the mixture is cured using a high intensity ultraviolet lamp.

The crosslinked structure helps to retain the lubricant(s) on surfaces to which the coating is applied.

The lubricious coatings according to the invention find utility in the medical device industry, in particular for medical devices inserted in the body. For example, the lubricious coatings find utility on catheter devices, in particular, on guide wires, catheter shafts, dilatation balloons, stent retaining sleeves and so forth.

Dilatation balloons may be coated on the body, cone and/or waist portions or any combination thereof. In some embodiments, the balloon is coated on the distal and proximal waist cones, and on a portion of the body, but not in the center of the body. This has been found to reduce "watermelon seeding", a term of art used to refer to slippage of the balloon during inflation in a lesion. This can be an issue in particular when the lesion is tapered, but this is not the only situation where "watermelon seeding" can occur.

The lubricity of the coating may be controlled through the use of different lubricants, as well as by the amount of lubricant added to the mixture. This can also allow for the use of different coatings on the same medical device such as different coatings on different portions of a catheter device where higher or lower lubricity may be desirable. For example, it may be desirable to coat the proximal portion of the catheter device with a less lubricious formula for better gripping, and to coat the distal portion of the device with a more highly lubricious coating for better trackability. This may be advantageous for guide wires or PV catheter assemblies.

The coating according to the present specification may be employed for drug delivery. A drug can be incorporated into the polymer network formed by the crosslinked material which helps to entrap a drug(s) which can then more slowly leach out of the crosslinked network when the medical device is employed in the body.

The following non-limiting examples further illustrate the present invention.

EXAMPLES

Example 1

TABLE 1

| | | | |
|---|---|---|---|
| Isopropyl alcohol | | Solvent | 77.7 wt-% |
| Polyethylene oxide Mw = 1,000,000 g/mole | | Lubricant | 1.8 wt-% |
| Reverse osmosis water | | | 19.765 wt-% |
| Ethoxylated trimethylol propane triacrylate | Sartomer SR-9035 (completely soluble) | crosslinker | 0.2 wt-% |
| Acrylic | Modaflow AQ 3025 | Flow modifier | 0.1 wt-% |
| Silane | | Coupling agent | 0.025 wt-% |
| 2-methyl 1-[4-methylthio) phenyl] 2-morpholinopropan-1-one | I-907 | Photoinitiator | 0.015 wt-% |

The above disclosure is intended to be illustrative and not exhaustive. This description will suggest many variations and alternatives to one of ordinary skill in this art. All these alternatives and variations are intended to be included within the scope of the claims where the term "comprising" means "including, but not limited to". Those familiar with the art may recognize other equivalents to the specific embodiments described herein which equivalents are also intended to be encompassed by the claims.

The invention claimed is:

1. A lubricious composition suitable for use on medical device comprising at least one polymerizable alkoxylated (meth)acrylate compound having at least two acrylate groups per molecule of the compound and a water solubility of about 15% or greater, said polymerizable alkoxylated (meth)acrylate is a member selected from the group consisting of alkoxylated trimethylol alkane tri(meth)acrylates, alkoxylated neopentyl glycol di(meth)acrylates, alkoxylated pentaerythritol tetra(meth)acrylates, trimethylolpropane ethoxylate (1 EO/OH) methyl ether di(meth)acrylate, aromatic alkoxylated (meth) acrylates having a water solubility of about 15% or greater, and mixtures thereof, and at least one second component which provides lubricity when wet.

2. The lubricious composition of claim 1 wherein said at least one polymerizable. alkoxylated (meth)acrylate compound has a water solubility of about 50% or greater.

3. The lubricious composition of claim 1 wherein said at least one polymerizable alkoxylated (meth)acrylate compound is a monomer.

4. The lubricious composition of claim 1 wherein said at least one polymerizable alkoxylated (meth)acrylate compound has a molecular weight of about 1000 g/mole or less.

5. The lubricious composition of claim 1 wherein said at least one polymerizable alkoxylated (meth)acrylate compound has at least three (meth)acrylate groups per molecule.

6. The lubricious composition of claim 1 wherein said at least one polymerizable alkoxylated (meth)acrylate compound has about 1 to about 20 moles alkoxylate.

7. The lubricious composition of claim 1 wherein said at least one polymerizable alkoxylated (meth)acrylate compound has about 2 to about 18 moles alkoxylate.

8. The lubricious composition of claim 1 wherein said at least one polymerizable alkoxylated (meth)acrylate compound has 3 to about 15 moles alkoxylate.

9. The lubricious composition of claim 1 wherein said at least one polymerizable alkoxylated (meth)acrylate compound is a non-aromatic alkoxylated (meth)acrylate compound.

10. The lubricious composition of claim 1 wherein said at least one polymerizable alkoxylated (meth)acrylate compound is an alkoxylated trimethylol propane triacrylate.

11. The lubricious composition of claim 1 wherein said alkoxylated trimethylol propane triacrylate is an ethoxylated trimethylol propane triacrylate.

12. The lubricious composition of claim 1 further comprising at least one photoinitiator.

13. The lubricious composition of claim 12 wherein said at least one photoinitiator is a member selected from the group consisting of benzophenones, aromatic-aliphatic ketones, α-amino ketones, benzil ketals, derivatives thereof, and mixtures thereof.

14. The lubricious composition of claim 13 wherein said at least one photoinitiator is 2, 2-dimethoxy-2-phenyl acetophenone.

15. The lubricious composition of claim 13 wherein said at least one photoinitiator is 2-methyl1-[4-methylthio)phenyl] 2-morpholinopropan-1-one, 2-benzyl-2-(dimethylamine)-1-[4morpholinyl)phenyl]-1 -butanone or mixture thereof.

16. The lubricious composition of claim 13 further comprising an acrylated amine synergist.

17. The lubricious composition of claim 1 wherein said at least one second component is hydrophilic.

18. The lubricious composition of claim 1 wherein said at least one second component is selected from the group consisting of polyalkylene glycols, alkoxy polyalkylene glycols, poly((meth)acrylic acids), polyvinylalcohols, poly(meth) acrylamides, polyurethanes, polyvinylsulfonic acids, poly (sodium styrenesulfonates), poly (sodium vinylsulfonates), poly(3 -hydroxybutyric acids), polyvinylpyrrolidones, polymers of hydroxyl-substituted lower alkyl (meth)acrylates, polyamides, polyethyleneirnines, copolymers thereof, and mixtures thereof.

19. The composition of claim 18 wherein said at least one second component is a polyurethane.

20. The composition of claim 19 wherein said at least one second component is an aliphatic polyether polyurethane.

21. The composition of claim 20 wherein said aliphatic polyether polyurethane is capable of absorbing about 5 times to about 21 times its own weight in water.

22. The lubricious composition of claim 17 wherein said at least one second component is polyethylene oxide, polyvinylalcohol, polyvinylpyrrolidone, polyurethane, or mixtures thereof.

23. The lubricious composition of claim 1 wherein said at least one second component has a molecular weight of about 50,000 to about 1,500,000 g/mole.

24. The lubricious composition of claim 1 wherein said at least one second component has a weight-average molecular weight of about 75,000 to about 1,000,000 g/mole.

25. The lubricious composition of claim 1 further comprising at least one member selected from the group consisting of fillers, flow modifiers, antioxidants, coupling agents, adhesion promoters, surfactants, and mixtures thereof.

26. The lubricious composition of claim 25 further comprising at least one flow modifier which is an acrylic flow modifier.

27. The lubricious composition of claim 25 further comprising at least one coupling agent which is a silane.

28. The composition of claim 1 crosslinked by actinic radiation.

29. A lubricious composition that has been cured by actinic radiation, said lubricious composition comprising:
  a) at least one lubricious hydrophilic polymer; and
  b) at least one polymerizable alkoxylated (meth)acrylate having two or more acrylate groups wherein said at least one polymerizable alkoxylated (meth)acrylate has about 15 wt-% water solubility or greater; said polymerizable alkoxylated (meth)acrylate is a member selected from the group consisting of alkoxylated trimethylol alkane tri(meth)acrylates, alkoxylated neopentyl glycol di(meth)acrylates, alkoxylated pentaerythritol tetra (meth)acrylates, trimethylolpropane ethoxylate (1 EO/OH) methyl ether di(meth)acrylate, aromatic alkoxylated (meth) acrylates,
  wherein said composition is cured by actinic radiation.

30. The lubricious composition of claim 29 wherein said at least one polymerizable alkoxylated (meth)acrylate is non-aromatic.

31. The lubricious composition of claim 29 wherein said at least one polymerizable alkoxylated (meth)acrylate has greater than about 50 wt-% water solubility.

32. The lubricious composition of claim 29 wherein said at least one polymerizable alkoxylated (meth)acrylate has about 1 to about 20 moles of alkoxylation.

33. The lubricious composition of claim 32 wherein said alkoxylation is ethoxylation.

34. The lubricious composition of claim 29 wherein said at least one polymerizable alkoxylated (meth)acrylate is an ethoxylated trimethylol propane triacrylate.

35. The lubricious composition of claim 29 wherein said at least one lubricious polymer is a hydrogel.

36. The lubricious composition of claim 29 wherein said at least one lubricious polymer is selected from the group consisting of polyalkylene glycols, alkoxy polyalkylene glycols, polyalkylene oxides, poly((meth)acrylic acids), polyvinylalcohols, poly(meth)acrylamides, polyurethanes, polyvinylsulfonic acids, poly(sodium styrenesulfonates), poly (sodium vinylsulfonates), poly(3-hydroxybutyric acids), polyvinylpyrrolidones, polymers of hydroxyl-substituted lower alkyl (meth)acrylates, polyamides, polyethyleneimines, copolymers thereof, and mixtures thereof.

37. The lubricious composition of claim 29 wherein said composition is curable by ultraviolet radiation, said composition further comprising at one free radical photoinitiator.

38. The lubricious composition of claim 37 wherein said at least one photoinitiator is a benzophenone, aromatic-aliphatic ketones, α-amino ketones, benzil ketals, derivatives thereof, and mixtures thereof.

39. The lubricious composition of claim 38 wherein said at least one photoinitiator is 2-dimethoxy-2-phenyl acetophenone.

40. The lubricious composition of claim 38 wherein said at least one photoinitiator is 2-methyl 1-[4-methylthio) phenyl] 2-morpholinopropan-1-one, 2-benzyl-2-(dimethylamine)-1-[4-morpholinyl)phenyl]-1-butanone or mixture thereof.

41. The lubricious composition of claim 38 further comprising an acrylated amine synergist.

42. The lubricious composition of claim 29 further comprising at least one additive selected from the group consisting of flow modifiers, coupling agents, antioxidants, surfactants and mixtures thereof.

43. The lubricious composition of claim 29 wherein said composition is admixed in a solvent or cosolvent blend.

44. The lubricious composition of claim 29 disposed on the surface of a medical device or on the surface of a component thereof said composition is cured.

45. The lubricious composition of claim 44 wherein said medical device or component thereof is a catheter shaft, dilatation balloon, guide wire lumen, guide wire or a stent retaining sleeve.

* * * * *